(12) United States Patent
Meretei

(10) Patent No.: US 7,947,074 B2
(45) Date of Patent: May 24, 2011

(54) IMPLANTABLE PROSTHETIC VALVE

(76) Inventor: Attila Meretei, Pompano Beach, FL (US)

( * ) Notice: Subject to any disclaimer, the term of this patent is extended or adjusted under 35 U.S.C. 154(b) by 52 days.

(21) Appl. No.: 12/158,747

(22) PCT Filed: Dec. 22, 2006

(86) PCT No.: PCT/US2006/048799
§ 371 (c)(1),
(2), (4) Date: Feb. 13, 2009

(87) PCT Pub. No.: WO2007/075892
PCT Pub. Date: Jul. 5, 2007

(65) Prior Publication Data
US 2009/0276039 A1    Nov. 5, 2009

Related U.S. Application Data

(60) Provisional application No. 60/753,716, filed on Dec. 23, 2005.

(51) Int. Cl.
*A61F 2/24* (2006.01)
*A61F 2/06* (2006.01)

(52) U.S. Cl. ..................................... 623/2.14; 623/1.25

(58) Field of Classification Search .................. 623/1.24, 623/2.1–2.24
See application file for complete search history.

(56) References Cited

U.S. PATENT DOCUMENTS

| | | | |
|---|---|---|---|
| 3,671,979 A | 6/1972 | Mouloupoulos | |
| 3,867,190 A | 2/1975 | Schmit | |
| 6,113,636 A | 9/2000 | Ogle | |
| 6,494,909 B2 * | 12/2002 | Greenhalgh | 623/1.24 |
| 7,569,071 B2 * | 8/2009 | Haverkost et al. | 623/1.24 |
| 7,670,368 B2 * | 3/2010 | Hill et al. | 623/1.24 |
| 2003/0139805 A1 | 7/2003 | Holmberg et al. | |
| 2003/0171805 A1 * | 9/2003 | Berg et al. | 623/2.14 |
| 2004/0092858 A1 * | 5/2004 | Wilson et al. | 604/9 |
| 2004/0167619 A1 * | 8/2004 | Case et al. | 623/1.34 |
| 2004/0186558 A1 | 9/2004 | Pavenik et al. | |
| 2004/0186563 A1 * | 9/2004 | Lobbi | 623/2.11 |
| 2005/0137701 A1 * | 6/2005 | Salahieh et al. | 623/2.38 |
| 2006/0111773 A1 * | 5/2006 | Rittgers et al. | 623/1.24 |
| 2006/0253188 A1 * | 11/2006 | Case | 623/1.24 |
| 2008/0200977 A1 * | 8/2008 | Paul et al. | 623/1.24 |
| 2010/0005658 A1 * | 1/2010 | Haverkost et al. | 29/890.12 |
| 2010/0131055 A1 * | 5/2010 | Case et al. | 623/2.17 |
| 2010/0185274 A1 * | 7/2010 | Moaddeb et al. | 623/1.24 |
| 2010/0191320 A1 * | 7/2010 | Straubinger et al. | 623/1.15 |

OTHER PUBLICATIONS

International Searching Authority, "International Search Report and Written Opinion", Jun. 11, 2008, 10 pages.

* cited by examiner

*Primary Examiner* — Suzette J Gherbi
(74) *Attorney, Agent, or Firm* — Fleisler Meyer LLP

(57) ABSTRACT

An implantable prosthetic valve for regulating fluid flow through a body vessel is provided. The prosthetic valve comprises an anchoring member, at least one leaflet, and a restraining member capable of temporarily preventing substantial movement of the leaflet between and open and closed position so as to allow fluid flow in the antegrade and retrograde directions. In various embodiments, the prosthetic valve reduces the risk of thrombosis. In various embodiments, the prosthetic valve reduces the appearance of potentially thrombogenic abnormal flow patterns at the site of implantation immediately following the implantation, allows cell deposition making the valve more biocompatible, less thrombogenic before flow changes resulting from valving action set in and allows tissue growth so that a partially or completely biological functioning valve may form on the scaffold provided by the implant.

25 Claims, 8 Drawing Sheets

IMPLANTABLE PROSTHETIC VALVE

BACKGROUND OF THE INVENTION

Prosthetic valves have proven to be a most beneficial treatment option in replacing diseased or malfunctioning native valves. Over the years, prosthetic heart valves have saved hundreds of thousands of lives. Prosthetic venous valves promise a treatment option for a large group of patients suffering from the consequences of lost or damaged valves, for example, in their deep veins.

Native valves have leaflets that act as one-way check valve and open to permit fluid flow through vessels in the forward or antegrade direction and close to substantially prevent fluid flow in a reverse or retrograde direction. Leaflets can change from an open position in response to a variety of circumstances, including changes in the cross-sectional shape of the vessel, and the fluid pressure within the vessel.

Unfortunately, native valves may lose their effectiveness leading to potentially life threatening conditions. For example, over time, the vessel wall may stretch, or the leaflet may become damaged due to disease or occlusion affecting the valve leaflet's ability to close resulting in changes in fluid flow, which may lead to, in severe cases, the insufficiency of the venous system of a limb and the pain, swelling, ulcers, thrombosis, a loss of quality of life, disability and even death.

In the past, conventional prosthetic valves have been designed to mimic native valving function as soon as they are implanted. That is, immediately after the valve is implanted in the body, the leaflets open at a certain fluid pressure and close at a certain pressure to prevent fluid flow in the retrograde direction. Indeed, most prior art valves have been designed to prevent fluid flow in the retrograde direction. A conventional prosthetic valve that stayed restrained in one position regardless of the fluid pressure would be considered defective and, if implanted in the body, may need to be removed.

By designing prosthetic valves to start their valving function immediately after they are implanted, gross fluid flow changes are promoted contributing to the formation of abnormal (e.g. turbulent) flow and thrombi (blood clots) at or around the site of implantation. Other factors that may lead to thrombosis include excessive trauma to the vessel's intima during implantation and the particular materials used to make the valve that may be thrombogenic. These factors (e.g., gross flow changes that may include thrombogenic turbulent flow, thrombogenicity of the valve, and trauma to the implantation site) all reduce prosthetic valve survival. Indeed, today there is no commonly accepted and widely used prosthetic venous valve available to the practicing physician, as most valve designs fail after implantation, primarily due to thrombosis (blood clot formation).

Minimally invasive percutaneous, and interventional techniques used to place the prosthetic valve at the implant site, sophisticated interventional devices such as catheters and delivery systems, as well as medical therapies applied in conjunction with the interventional approach, have been developed to reduce trauma to the vessel and in turn reduce the risk of thrombosis and thus increase prosthetic valve survival.

New implantable prosthetic valves and methods are still needed that delay gross flow changes and the development of abnormal, thrombogenic flow patterns that immediately follow the implantation of prosthetic valves of conventional designs.

SUMMARY OF THE INVENTION

Prosthetic valves and methods are provided that delay the commencement of valving function and allow for a period of time in which the native vessel heals and recuperates after the intervention and before flow changes brought about by functioning valve leaflets set in.

In various embodiments, the prosthetic valve and methods allow for natural growth of cells and tissue over the implanted prosthesis, which may reduce the implant's thrombogenicity and, in turn, may increase prosthetic valve survival by limiting the presence of key thrombogenic factors (e.g. flow changes leading to abnormal thrombogenic flow patterns, implant thrombogenicity) in the time period immediately following prosthetic valve implantation.

In various embodiments, the prosthetic valve becomes more biocompatible by allowing cell deposition, tissue growth and remodeling into a partially or completely biological functioning valve.

In one embodiment, an implantable prosthetic valve for regulating fluid flow through a body vessel is provided, comprising: an anchoring member having exterior and interior surfaces, the exterior surface of the anchoring member capable of contacting an inner wall of the body vessel, the interior surface of the anchoring member defining an opening for fluid flow in an antegrade and a retrograde direction; at least one leaflet having a first edge attached to the anchoring member and a second edge being moveable between a first position and a second position, the first position substantially permits fluid flow in the antegrade direction and the second position substantially prevents the fluid flow in the retrograde direction; and a restraining member contacting the second edge of the at least one leaflet, the anchoring member, and/or vessel wall, the restraining member capable of temporarily preventing substantial movement of the at least one leaflet between the first position and the second position so as to allow fluid flow in the antegrade and retrograde directions.

In another embodiment, an implantable prosthetic valve for regulating fluid flow through a body vessel is provided, comprising: an anchoring member having exterior and interior surfaces, the exterior surface of the anchoring member capable of contacting an inner wall of the body vessel, the interior surface of the anchoring member defining an opening for fluid flow in an antegrade and a retrograde direction; at least one leaflet having a first edge attached to the anchoring member and a second edge being moveable between a substantially open position and a substantially closed position, the open position substantially permits fluid flow and the closed position substantially prevents fluid flow; and a restraining member contacting the second edge of the at least one leaflet, the restraining member capable of temporarily holding the at least one leaflet in the substantially open position to allow fluid flow.

In yet another embodiment, a kit for implanting a prosthetic valve is provided, comprising: an anchoring member having exterior and interior surfaces, the exterior surface of the anchoring member capable of contacting an inner wall of the body vessel, the interior surface of the anchoring member defining an opening for fluid flow in an antegrade and a retrograde direction; at least one leaflet having a first edge attached to the anchoring member and a second edge being moveable between a first position and a second position, the first position substantially permits fluid flow in the antegrade direction and the second position substantially prevents the fluid flow in the retrograde direction; a restraining member for contacting the second edge of the at least one leaflet, the anchoring member and/or vessel, the restraining member capable of temporarily preventing substantial movement of the at least one leaflet between the first position and the second position so as to allow fluid flow in the antegrade and retrograde directions; packaging for the implantable prosthetic valve; and instructions for implanting the prosthetic valve.

In one exemplary embodiment, an implantable prosthetic valve leaflet for regulating fluid flow through a body vessel is provided, the leaflet comprising a first edge and a second edge, the first edge capable of being attached to a wall of the body vessel, and/or an anchoring member, the second edge of the leaflet having a restraining member capable of temporarily restraining the second edge of the leaflet against the wall of the body vessel and/or anchoring member so as to substantially prevent movement of the leaflet between a first position and a second position. This embodiment may entirely eliminate the need for an anchoring member, thereby simplifying the design, in that the leaflet's first edge may be directly and permanently attached to the vessel wall without the use of an anchoring member, by such means as sutures, barbs, hooks, staples, biocompatible adhesives and the like.

In another exemplary embodiment, a method is provided of implanting a prosthetic valve within a blood vessel at a desired position therein, comprising: a) providing a prosthetic valve which comprises: (i) an anchoring member having exterior and interior surfaces, the interior surface of the anchoring member defining an opening for blood flow in an antegrade and a retrograde direction; (ii) at least one leaflet having a first edge attached to the anchoring member and a second edge being moveable between a first position and a second position, the first position substantially permits blood flow in the antegrade direction and the second position substantially prevents blood flow in the retrograde direction; b) forming an opening in the blood vessel; c) inserting the valve through the formed opening and delivering the valve to the desired position at which the valve is to be implanted and implanting the valve so that the exterior surface of the anchoring member is substantially coincident with a portion of an inner wall of the blood vessel; d) restraining the second edge of the at least one leaflet with a restraining member to temporarily prevent substantial movement of the at least one leaflet between the first position and the second position so as to allow blood flow in the antegrade and retrograde directions; e) allowing the vessel to heal after the valve is implanted; and f) later removing the restraining member or allowing the restraining member to be removed by the body so that the second edge of the leaflet is moveable between the first position to permit blood flow in the antegrade direction and the second position to substantially prevent blood flow in the retrograde direction.

In yet another exemplary embodiment, a method is provided of implanting a prosthetic valve within a blood vessel at a desired position therein, comprising: a) providing a prosthetic valve which comprises: at least one leaflet having a first edge attachable to the vessel wall and a second edge being moveable between a first position and a second position, the first position substantially permits blood flow in the antegrade direction and the second position substantially prevents blood flow in the retrograde direction; b) forming an opening in the blood vessel; c) inserting the valve through the formed opening and delivering the valve to the desired position at which the valve is to be implanted and implanting the valve so that the at least one leaflet is attached to the inner wall of the blood vessel; d) restraining the second edge of the at least one leaflet with a restraining member to temporarily prevent substantial movement of the at least one leaflet between the first position and the second position so as to allow blood flow in the antegrade and retrograde directions; e) allowing the vessel to heal after the valve is implanted; and f) later removing the restraining member or allowing the restraining member to be removed by the body so that the second edge of the leaflet is moveable between the first position to permit blood flow in the antegrade direction and the second position to substantially prevent blood flow in the retrograde direction.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

Figure 1:
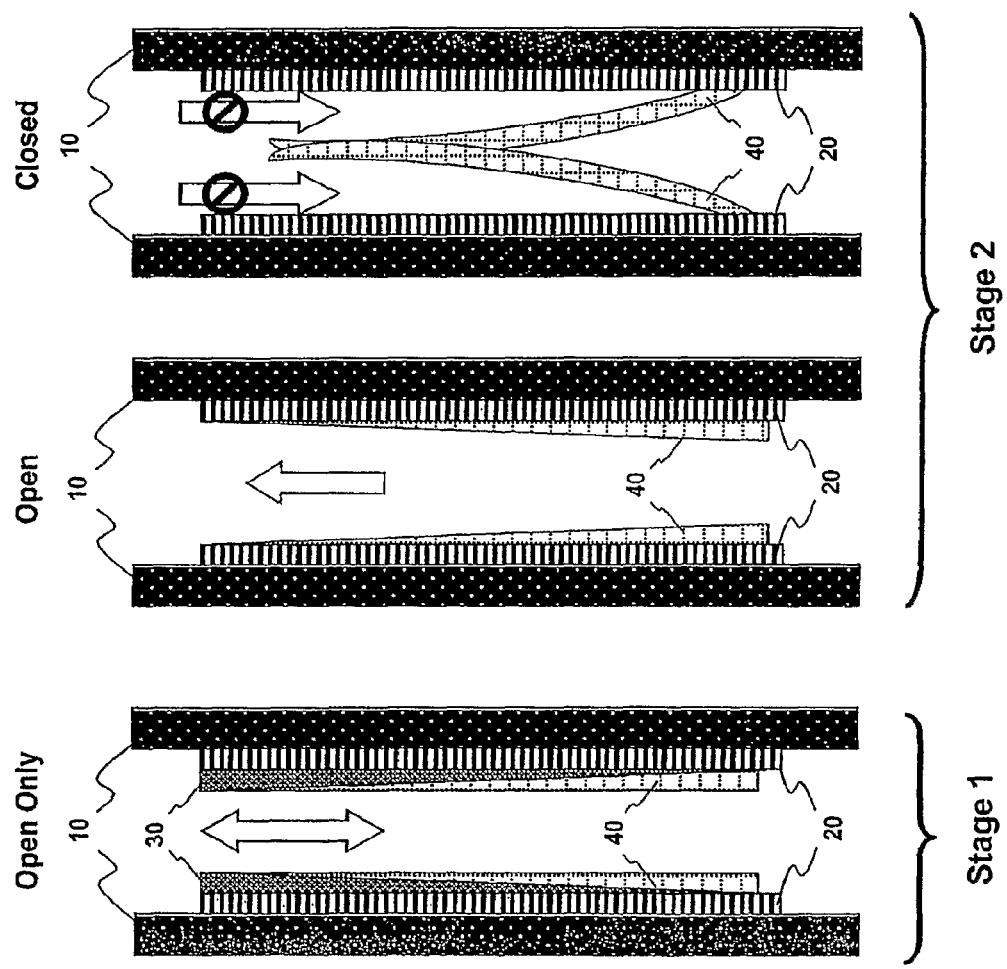
FIG. 1 illustrates a partially sectional view of a body vessel with the prosthetic valve implanted within the vessel 10. The prosthetic valve comprises anchoring members 20, leaflets 40, and restraining members 30 that temporarily hold the leaflets open allowing both-antegrade (forward) and retrograde (reverse) flow of fluid (indicated by the arrow in stage 1). This design reduces flow changes at the site of implantation while the at least one leaflet is restrained in the first position, and therefore reduces the appearance of potentially thrombogenic abnormal flow patterns, allows cell deposition making the valve more biocompatible, less thrombogenic before flow changes resulting from the at least one leaflet's valving action set in and allows tissue growth so that a partially or completely biological functioning valve may form on the scaffold provided by the implant. In this view, the anchoring members are approximately the same length as the leaflet. In stage 2, after the restraining members 30 are removed (naturally by the body or through a procedure) the valve can now freely open and close as a native valve.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION OF THE INVENTION

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents, which may be included within the invention as defined by the appended claims.

It is noted that, as used in this specification and the appended claims, the singular forms "a," "an," and "the," include plural referents unless expressly and unequivocally limited to one referent. Thus, for example, reference to "a leaflet" includes one, two, three or more leaflets.

The headings below are not meant to limit the disclosure in any way; embodiments under any one heading may be used in conjunction with embodiments under any other heading.

In various embodiments of the present invention, an implantable prosthetic valve for regulating fluid flow through a body vessel is provided, comprising: an anchoring member having exterior and interior surfaces, the exterior surface of the anchoring member capable of contacting an inner wall of the body vessel, the interior surface of the anchoring member defining an opening for fluid flow in an antegrade and a retrograde direction; at least one leaflet having a first edge attached to the anchoring member and a second edge being moveable between a first position and a second position, the first position substantially permits fluid flow in the antegrade direction and the second position substantially prevents the fluid flow in the retrograde direction; and a restraining member contacting the second edge of the at least one leaflet or the anchoring member, the restraining member capable of temporarily preventing substantial movement of the at least one leaflet between the first position and the second position so as to allow fluid flow in the antegrade and retrograde directions.

In various embodiments, the prosthetic valve comprises one or multiple (e.g., two, three, four or more) leaflets, anchoring members, and/or restraining members.

Anchoring Members

The anchoring member 20, which is illustrated in FIGS. 1-7, is designed to hold the implant securely in place, attached to the vessel wall at the site of implantation, prevent tilting and migration, contribute to desirable flow characteristics in and around the implant, allow cell deposition, tissue growth and reduce the risk of thrombosis. In various embodiments, the anchoring member has a biotextured surface structure which promotes cell adhesion, enhance tissue growth, and increases electrical-charge transfer. Such surface structures (e.g., porosity, granulation, grooves, channels, etc.) can be on the nanometer or micron scale, in accordance with the sizes of mammalian cells and can be manufactured by, for example, various surface structuring techniques including, but not limited to ion beam texturing, abrasive grit blasting, atomic oxygen texturing, chemical etching as well as deposition or microfabrication technologies all which may improve surface energy, charge and chemistry that is amenable to cell deposition and tissue growth.

The anchoring member comprises internal and external surfaces. The internal surface of the anchoring member defines an opening that allows fluid flow in antegrade and retrograde directions. Typical vessel diameters for fluid flow depend on the type of vessel. For blood vessels, the typical diameter of the openings in the anchoring member can be from about 0.3 mm to about 30 mm. These openings may be substantially: round, square, triangular, ovoid and/or teardrop-shaped. The external surface of the anchoring member is attached to the wall of the vessel, for example, the lumen. In various embodiments, the external surface of the anchoring member attaches to the inner wall of the blood vessel and allows tissue growth from the vessel wall and cell deposition from blood flow, effectively integrating the anchoring member into the vessel wall over time (e.g., generally measured in weeks) and making the valve more biocompatible. These processes reduce the risk of thrombosis by making the valve more biocompatible.

A wide variety of anchoring members can be utilized as long as the anchoring member provides a surface for the at least one leaflet to be attached and anchors the valve to the inner wall of the vessel to prevent migration of the valve within the vessel. In various embodiments, the anchoring member comprises stents, barbs, clips, latch, staples, rivets, adhesives, sutures, tissue welding, weaves, cross-links, and the like that retain the anchoring member to the inner wall of vessel 10, shown in FIG. 1-7, at the site of implantation for a period of time to allow the tissue growth and/or the vessel to heal.

Suitable anchoring members can also have a variety of shapes and configurations, including braided strands, helically, tubular, wound strands, ring members, consecutively attached ring members, zigzag members, tubular members, and anchoring members cut from tubes.

In various embodiments, the anchoring member has radially compressed and radially expanded support frame configurations. Such an anchoring member can be implanted at a point of treatment within a body vessel by minimally invasive techniques, such as a delivery and deployment through an intravascular catheter. In various embodiments, the entire prosthetic valve can be compressed in a delivery system and when deployed at the implant site, expands to the diameter of the vessel. For example, the anchoring member can provide a stenting function, e.g., exert a radially outward force on the interior wall of a vessel at the point of implantation in the body, or deform the vessel at the site of implantation and create a venous sinus-like widening of the vessel around the leaflet members.

The anchoring member chosen for the valve will depend on numerous factors, including the body vessel in which the valve is being implanted or deployed, the axial length of the implantation site within the vessel, the number of leaflets desired (e.g., monocuspid, bicuspid, tricuspid), the inner diameter of the vessel, the delivery method for placing the valve, and other considerations. Those of ordinary skill in the art can determine an appropriate anchoring member based on these and other considerations.

For example, the anchoring member can be self-expanding or balloon expandable. The structural characteristics of both of these types of anchoring members are known in the art. Each type of anchoring member has advantages and for any given application, one type may be more desirable than the other based on a variety of considerations. For example, in the peripheral vasculature, vessels are generally more compliant and typically experience dramatic changes in their cross-sectional shape during routine activity. Prosthetic valves for implantation in the peripheral vasculature should retain a degree of flexibility to accommodate these changes of the vasculature. Accordingly, prosthetic valves intended for implantation in the peripheral vasculature, such as prosthetic venous valves, advantageously include a self-expanding anchoring member. These anchoring members, are known in the art, and are generally more flexible than balloon-expandable anchoring members following deployment.

In various embodiments, the anchoring member has disposed thereon a restraining member. The restraining member can then contact the free edge of the leaflet to restrain the leaflet in substantially the first or open position.

In various embodiments, the anchoring member comprises at least one metal, biological material, biocompatible material, bioremodellable material, bioabsorbable/biodegradable material, extracellular matrix material, and/or synthetic material (e.g., polymers). Suitable polymers include such materials as Dacron, PTFE, polyurethane, silicone and the like. In various embodiments, these materials may also be disposed on or imbedded in the leaflet as a coating or thin film.

The anchoring member may comprise biological materials, such as material obtained from tissues of human donors, the patient's own tissues (autologous grafts), or of animals (e.g., xenografts). Cells may be extracted from these tissues to form an extracellular matrix material. Examples of extracellular matrix material include, but are not limited to, bioremodellable preparations of small intestinal submucosa (SIS), pericardium, stomach submucosa, liver basement membrane, urinary bladder submucosa, tissue submucosa, collagen, and/or dura mater. These materials are particularly suitable for the anchoring member because they allow cell deposition and growth of tissue, yet are strong enough to provide support for the leaflet and/or restraining member.

Preferably, the material used to construct the anchoring member is biocompatible and/or bioabsorbable/biodegradable. Biocompatible materials are those that the body generally accepts without a major immune, inflammatory or toxic response, such as thrombosis. Bioabsorbable or biodegradable material serves its intended function after implantation and then is absorbed by the body or disintegrates and subsequently is excreted from the body. Typically, bioabsorbable or biodegradable materials have mechanical properties that match the vessel, remain sufficiently strong until the surrounding tissue has healed, do not invoke a major immune, inflammatory or toxic response, demonstrate acceptable shelf life and, in various embodiments, are easily sterilized. When the bioabsorbable or biodegradable material is a polymer, factors affecting the mechanical performance of bioabsorbable or biodegradable polymers are those that are well known to the one of ordinary skill in the art and include, for example, monomer selection, the polymer's hydrophilicity or hydrophobicity, molecular weight, molecular-weight distribution, end groups, sequence distribution (random versus blocky), and presence of residual monomer or additives. Typically, bioabsorbtion is accomplished by synthesizing polymers that have hydrolytically unstable linkages in the backbone. The most common chemical functional groups with this characteristic are esters, anhydrides, orthoesters, and amides.

Suitable bioabsorbable or biodegradable materials include poly-alpha hydroxy acids such as polylactic acid, polylactide, polyglycolic acid (PGA), or polyglycolide; trimethlyene carbonate; polycaprolactone; expanded polytetrafluoroethylene, poly-beta hydroxy acids such as polyhydroxybutyrate or polyhydroxyvalerate; or other polymers such as polyphosphazines, polyorganophosphazines, polyanhydrides, polyesteramides, polyorthoesters, polyethylene oxide, polyesterethers (e.g., polydioxanone) or polyamino acids (e.g., poly-L-glutamic acid or poly-L-lysine). There are also a number of naturally derived resorbable polymers that may be suitable, including modified polysaccharides, such as cellulose, chitin, and dextran, and modified proteins, such as fibrin and casein. In various embodiments, the bioabsorbable or biodegradable material is a hydrogel that serves as a scaffold for the prosthetic valve.

Examples of metals suitable for use in the anchoring member include, but are not limited to, molybdenum alloys, stainless steel, spring steel (e.g. Elgiloy®), shape memory alloy, and/or nitinol, which are considered desirable materials for use in the anchoring member due at least to their biocompatibility, shapeability, and well-characterized nature. In various embodiments, the metal is biocompatible and reduces the risk of thrombosis. Non-metals such as silicon, pyrolitic carbon and/or superelastic materials can be used alone or in combination with polymers, metals and/or biological materials. In various embodiments, the anchoring member is seeded or cultured with cells (e.g., endothelial cells, smooth muscle cells) and factors or substances to enhance adhesion to the anchoring member, such as integrins (RGD peptides), that enhance spreading and growth of cells, making the valve more biocompatible and thus reducing thrombosis. Vascular endothelial growth factor (VEGF), Tie2/Ang, and Eph/ephrin families of growth factors can also be used for adhesion, spreading and growth of the cells. Particularly, preferred polymers for seeding of cells include, but are not limited to, polytetrafluoroethylene (PTFE), ePTFE/denucleated ePTFE, polyester, pHEMa/MMA copolymers, polyurethane, polyethyleneterepthalate (PET), poly(ether urethane urea) PEUU, perflurosulfonic acid, and the like.

The anchoring member may comprise at least one antithrombotic agent, anticoagulant, antibiotic and/or antinflammatory agent. Suitable antithrombotic and anticoagulant agents include, but are not limited to, fluorine-acryl-styleneurethane-silicone, fluorinated carbon, polylactic acid, biodegradable polylactic acid (PLA) stent coating with an incorporated thrombin inhibitor and a platelet aggregation inhibitors, heparin, urokinase, phosphorylcholine, persulfated bD-mono and disaccharides, polyvynilpyrrolidone- and polyacrylamide-based synthetic passivating coatings, hydrophilic passivating coatings, albumin passivated coatings, plasminogen binding coatings, thrombomodulin, and the like. Suitable antibiotics include, but are not limited to, silver oxide or silver chloride containing coatings or coatings that elute antibiotics such as minocycline, tetracycline, rifampin, rapamycin, vancomycin, gentamicin, and the like. Suitable antiinflammatory agents include, but are not limited to, steroids, such as prednisone, dexamethasone, prednisolone, and the like, non-steroidal antinflammatory agents such as ibuprofen, ketoprofen, indomethacin, naproxen, aspirin, and the like.

The anchoring member may comprise at least one radiopaque material that enhances its visibility under fluoroscopy. Suitable materials include gold, platinum, barium sulfate, tantalum, and the like.

Leaflet

The prosthetic valve comprises at least one leaflet, which is designed to contribute to desirable flow characteristics in and around the implant, and has a surface structure, chemistry and charge that allows cell deposition, tissue growth and reduces the risk of thrombosis.

In various embodiments, the leaflet, like the anchoring member, has a biotextured surface structure which promotes cell adhesion, enhance tissue growth, and increases electrical-charge transfer. Such surface structures (e.g., porosity, granulation, grooves, channels, etc.) can be on the nanometer or micron scale, in accordance with the sizes of mammalian cells and can be manufactured by, for example, various surface structuring techniques including, but not limited to ion beam texturing, abrasive grit blasting, atomic oxygen texturing, chemical etching as well as deposition or microfabrication technologies all which may improve surface energy, charge and chemistry that is amenable to cell deposition and tissue growth.

In various embodiments, the leaflet 40, two are shown in FIGS. 1-8, has a first portion attached to the anchoring member and a second portion being moveable between a first or open position and a second or closed position, the first position substantially permits fluid flow in the antegrade direction and the second position substantially prevents fluid flow in the retrograde direction. The second edge of the leaflet is capable of being temporarily restrained by the restraining member to prevent substantial movement of the leaflet between the first or open position and the second or closed position so as to allow fluid flow in the antegrade and retrograde directions.

It is believed that allowance of both antegrade and retrograde flow after implantation of the prosthetic valve limits the pooling of blood around the valve during periods of low pressure, which can reduce the formation of thrombus around the valve leaflets and, therefore, increase the patency and effective lifetime of the valve. Additionally, it is believed that by allowing both antegrade and retrograde flow immediately after implantation of the valve has the benefits of reducing gross interruption of fluid flow and the creation of abnormal, thrombogenic flow patterns, enhancing cell deposition and tissue growth, all making the valve more biocompatible.

The leaflet has at least two surfaces. One surface of the leaflet faces antegrade fluid flow and the other surface faces retrograde blood flow. In prosthetic valve designs, one two, three or more leaflets substantially block all or most of the retrograde flow by allowing the pressure exerted by retrograde flow to move the free edges of the leaflet to a closed or second position so that the free edges coapt with one another in the case of two or more leaflets, in the case of one leaflet, the free edge will coapt with the anchoring member or the vessel wall to substantially block all or most of the retrograde flow. Antegrade flow will move the free edges of the leaflet members towards the vessel wall creating an opening or a flow channel between the leaflet members for uninhibited forward flow.

A wide variety of leaflets can be utilized as long as the leaflet is capable of being attached to the anchoring member or vessel wall and is capable of being temporarily restrained by the restraining member. The leaflets may be any suitable shape, including but not limited to, substantially: round, square, triangular, ovoid and/or teardrop-shaped.

The leaflet chosen for the valve will depend on numerous factors, including the body vessel in which the valve is being implanted, the implantation site within the vessel, the number of valves desired (e.g., monocuspid, bicuspid, tricuspid), the inner diameter of the vessel, the delivery method for placing the valve, and other considerations. Those of ordinary skill in the art can determine an appropriate anchoring member based on these and other considerations. In various embodiments, the valve employs one, two, three, four or more leaflets.

The leaflet may be attached to the anchoring member or the vessel wall by any suitable means. The particular means of attachment will depend on the material and construction of the anchoring member, leaflet and the restraining member. In various embodiments, the first part of the leaflet is attached to the anchoring member or directly to the vessel wall by hinge, joint, clip, latch, staple, rivet, adhesive, suture, tissue welding, weaving, cross-linking, and the like, or combination thereof.

In various embodiments, as with the anchoring member, the leaflet comprises at least one metal, biological material, biocompatible material, bioremodellable material, bioabsorbable/biodegradable material, and/or synthetic material (e.g., polymer). Suitable polymers include such materials as Dacron, PTFE, polyurethane, silicone and the like. In various embodiments, these materials may also be disposed on or imbedded in the leaflet as a coating or thin film.

The leaflet may comprise biological materials, such as material obtained from human donors, the patient's own tissues (e.g., autologous graft), or of tissues of animals (e.g., xenograft). Cells may be extracted from these tissues to form an extracellular matrix material. Examples of extracellular matrix material include, but are not limited to, bioremodellable material such as preparations of small intestinal submucosa (SIS), pericardium, stomach submucosa, liver basement membrane, urinary bladder submucosa, tissue submucosa, collagen, and/or dura mater. These materials are particularly suitable for the leaflet because they allow cell deposition and growth of tissue and are strong and resilient enough to perform valving function.

Examples of metals suitable for use in the leaflet include, but are not limited to, molybdenum alloys, stainless steel, spring steel (e.g. Elgiloy®), shape memory alloy, and/or nitinol, which are considered desirable materials for use in the leaflet due at least to their biocompatibility, shapeability, and well-characterized nature. In various embodiments, the metal is biocompatible and reduces the risk of thrombosis. Non-metals such as silicon, pyrolitic carbon and/or superelastic materials can be used alone or in combination with polymers, metals and/or biological materials.

In a preferred embodiment the leaflet is constructed of a metallic thin film, such as nitinol thin film. A nitinol thin film's characteristics of high tensile strength at a low thickness, flexibility, elasticity and biocompatibility are important benefits in the construction of artificial leaflets.

In various embodiments, like the anchoring member, the leaflet is seeded or cultured with cells (e.g., endothelial cells, smooth muscle cells) and factors or substances to enhance adhesion to the anchoring member, such as integrins (RGD peptide), which enhance spreading and growth of cells, making the valve more biocompatible and thus reducing thrombosis. Vascular endothelial growth factor (VEGF), Tie2/Ang, and Eph/ephrin families of growth factors can also be used for adhesion, spreading and growth of the cells.

Preferred polymers for seeding of cells (e.g., endothelial cells, smooth muscle cells) include, but are not limited to, polytetrafluoroethylene (PTFE), ePTFE/denucleated ePTFE, polyester, pHEMa/MMA copolymers, polyurethane, polyethyleneterepthalate (PET), poly(ether urethane urea) PEUU, perfluorosulfonic acid, and the like.

In various embodiments both the anchoring member and the leaflets are coated with a material or substance that enhances the natural process of cellular or tissue overgrowth, such as for example, drug eluting material, a hydrogel, SIS, pericardium, stomach submucosa, liver basement membrane, urinary bladder submucosa, tissue submucosa, collagen, and/or dura mater. For example, the anchoring member and the leaflet can be coated with a drug that enhances cellular or tissue overgrowth on the anchoring member and the leaflet. Other embodiments envisioned are where the anchoring member and leaflets are coated with a layer of SIS or other extracellular matrix or a synthetic material. These embodiments prompt or induce cellular or tissue growth on the valve and either allow the formation of a partially or completely biological functioning valve on the scaffold provided by the implant or at least make the implant more biocompatible and less thrombogenic.

In various embodiments, the leaflet, like the anchoring member, may comprise at least one antithrombotic agent, anticoagulant, antibiotic and/or antiinflammatory agent.

In various embodiments, the leaflet, like the anchoring member may comprise at least one radiopaque material that enhances its visibility under fluoroscopic imaging. Suitable materials include gold, platinum, barium sulfate, tantalum, and the like.

In various embodiments, the leaflet may have openings or porosity on a part or all of its surface to allow a controlled amount of reverse flow even in its second or closed position. This controlled reverse flow may prevent the pooling and stagnation of blood between the leaflet and the vessel wall, where such stagnating blood may form a thrombus.

In various embodiments, the second edge of the leaflet has a restraining member attached thereto to temporarily prevent substantial movement of the leaflet between the first position or open position and the second position so as to allow fluid flow in the antegrade and retrograde directions.

In various embodiments, the leaflet is substantially coincident with all or a portion of the interior surface of the anchoring member. For example, in various embodiments, the anchoring member and the leaflet may be formed as a one-piece construction and implanted into the vessel lumen. After implantation, allowing time for remodeling, the leaflet is released from this one-piece construction by creating and separating a free edge from the one-piece prosthetic valve so that the leaflet can now freely move in the first or open position and the second or closed position. In this embodiment, it is envisioned that a double-walled tube is implanted initially. The double-walled tube comprises two layers, an external layer and an internal layer. Both layers have two surfaces and external surface and an internal surface. After implantation, tissue growth into the external layer of the tube will incorporate the double-walled tube into the vessel wall. This external layer will function as the anchoring member for the prosthetic valve. The inner surface of the inner layer will also obtain an endothelial cover. Once this remodeling is accomplished, the two layers of the tube are separated along a line that corresponds to the free edge of a leaflet. The separation may be accomplished by cutting through the inner layer in an interventional procedure, (e.g., medical, surgical and/or percutaneous procedure). This approach is preferred as it also cuts though the endothelium and other tissue, if any, that grew over the separation line after implantation. Another means of achieving separation may be to trigger the decomposition of a material that was integrated into the inner layer of the tube specifically along the line where the separation was desired. This material may be sensitive to heat, light, RF frequency or another form of energy, or to a specific chemical that is used to trigger its degradation.

Restraining Member

The prosthetic valve comprises a restraining member 30, illustrated in FIGS. 1-8, which is designed to temporarily attach the leaflet to the anchoring member and/or vessel wall, reduce gross changes in fluid flow, and has a surface and charge that allows cell deposition, tissue growth and reduces the risk of thrombosis.

The restraining member contacts at least the second or free edge of leaflet to temporarily prevent substantial movement of the leaflet between the first or open position and the second or closed position so as to allow fluid flow in the antegrade and retrograde directions. In various embodiments, the restraining member contacts the entire leaflet and part or the entire surface of the anchoring member or the inner wall of the vessel to perform its restraining function.

In various embodiments, the restraining member can temporarily or releasably attach the retrograde flow-facing surface of the leaflet to the interior surface of the anchoring member. Alternatively, the restraining member may attach the leaflet's retrograde flow facing surface to the vessel wall. The restraining member temporarily suspends the movement of the leaflet's free edge. Thus, while the restraining member is in place, the leaflet will remain substantially stationary and its retrograde flow-facing surface is flush with the inner surface of the anchoring member or the vessel wall. With the restraining member in place the leaflet, the prosthetic valve will not block retrograde flow as the free edge of the leaflet can not substantially move to the second or closed position, or in a multi-leaflet design, the free edges of the leaflet members can not coapt. The leaflet thus is in a restrained position and this will have the benefit immediately after implantation that the flow through the prosthesis, and the vessel generally, will remain uninhibited. The flow remains largely unchanged after the prosthesis is delivered into the blood vessel and thus no potentially thrombogenic flow changes are created. Further, cell deposition and tissue growth can progress on both the anchoring member and the leaflet, preferably covering their surface with endothelium and rendering these surfaces non-thrombogenic. Ideally, the leaflet-restraining member remains in place until such remodeling is accomplished. After this period of approximately 4-8 weeks the leaflet-restraining member is removed, the free edge(s) of the leaflet member is released and the valve can perform its intended function of maintaining unidirectional flow (e.g., when open in substantially the antegrade direction and when closed substantially preventing retrograde flow).

The restraining member is temporarily attached to the anchoring member, vessel wall, and/or leaflet by any suitable means as long as it can be removed from the leaflet, anchoring member, and/or vessel wall so that the leaflet can move from the open and closed positions and perform its valving function. Removal of the restraining member can be accomplished by a medical or surgical intervention or naturally by the body. For example, the restraining member can comprise a biodegradable/bioresorbable material that serves its intended function after implantation and then disintegrates and subsequently is excreted from the body.

In various embodiments, the restraining member is biodegradable, heat, chemical, light degradable or degradable by other forms of energy such as by ultrasound or microwave. In one particularly preferred embodiment, the restraining member is a biodegradable/bioabsorbable adhesive that is coated on the leaflet or anchoring member and is removed by the body over time to allow the leaflets to perform native valving function.

In another particularly preferred embodiment, the leaflet-restraining member may comprise a hydrogel material that attaches the free edge of the leaflet, or the entire retrograde flow-facing surface of the leaflet to the anchoring member. The hydrogel may be bioabsorbable in the same time period required for surface remodeling of the anchor and leaflet. In which case, the hydrogel is naturally degraded releasing the leaflet to perform its valving function or the hydrogel may be removed by a second interventional, medical, percutaneous and/or surgical procedure or by heat, chemical, light or degradable by other forms of energy such as by ultrasound or microwave.

The particular means of attachment of the restraining member to the anchoring member, vessel wall and/or leaflet will depend on the material and construction of the anchoring member, leaflet and the restraining member. In various embodiments, the restraining member is attached to the leaflet, anchoring member and/or vessel wall by hinge, joint, clip, latch, staple, rivet, adhesive, suture, tissue welding, weaving, cross-linking, and the like.

A wide variety of restraining members can be utilized as long as the restraining member is capable of temporarily restraining the leaflet. Typical constructions of the restraining member include, but are not limited to, joint, hinge, clip, latch, barb, staple, stent, ring, rivet, adhesive, suture, tissue welding material, weave, cross-linked material, biological material, biocompatible material, bioabsorbable/biodegradable material, extracellular matrix material, adhesive, cement, synthetic material, metal or combinations thereof.

The restraining member, like the leaflet and the anchoring member, may comprise biological materials, such as material obtained from human donors, the patient's own tissues (e.g., autologous grafts), or of animals (e.g., xenografts). Cells may be extracted from these tissues to form an extracellular matrix material. Examples of extracellular matrix material include, but are not limited to, bioremodellable material such as preparations of small intestinal submucosa (SIS), pericardium, stomach submucosa, liver basement membrane, urinary bladder submucosa, tissue submucosa, collagen, and/or dura mater. These materials are particularly suitable for the restraining member because they are biocompatible and strong enough to effectively restrain the leaflets.

Preferably, the restraining member, like the anchoring member and leaflet, comprises material that is biocompatible and/or bioabsorbable/biodegradable. Suitable bioabsorbable or biodegradable materials include poly-alpha hydroxy acids such as polylactic acid, polylactide, polyglycolic acid (PGA), or polyglycolide; trimethlyene carbonate; polycaprolactone; expanded polytetrafluoroethylene, poly-beta hydroxy acids such as polyhydroxybutyrate or polyhydroxyvalerate; or other polymers such as polyphosphazines, polyorganophosphazines, polyanhydrides, polyesteramides, polyorthoesters, polyethylene oxide, polyester-ethers (e.g., polydioxanone) or polyamino acids (e.g., poly-L-glutamic acid or poly-L-lysine). There are also a number of naturally derived resorbable polymers that may be suitable, including modified polysaccharides, such as cellulose, chitin, and dextran, and modified proteins, such as fibrin and casein.

Examples of metals suitable for use as the restraining member include, but are not limited to, molybdenum alloys, stainless steel, spring steel (e.g. Elgiloy®), shape memory alloy, and/or nitinol, which are considered desirable materials for use in the restraining member due at least to their biocompatibility, shapeability, and well-characterized nature. In various embodiments, the metal is biocompatible and reduces the risk of thrombosis. Non-metals such as silicon, pyrolitic carbon and/or superelastic materials can be used alone or in combination with polymers (e.g. Dacron, PTFE, PET and the like), metals and/or biological materials.

In various embodiments, like the leaflet and anchoring member, the restraining member is seeded or cultured with cells (e.g., endothelial cells, smooth muscle cells) and factors or substances to enhance biological absorption processes or the adhesion to the anchoring member, such as integrins (RGD peptide), which allow spreading and growth of the cells, making the valve more biocompatible and thus reducing thrombosis. Vascular endothelial growth factor (VEGF), Tie2/Ang, and Eph/ephrin families of growth factors can also be used for adhesion, spreading and growth of the cells.

Preferred polymers for seeding of cells include, but are not limited to, polytetrafluoroethylene (PTFE), ePTFE/denucleated ePTFE, polyester, pHEMa/MMA copolymers, polyurethane, polyethyleneterephthalate (PET), poly(ether urethane urea) PEUU, perfluorosulfonic acid, and the like.

In various embodiments, the restraining member, like the anchoring member and leaflet, may comprise at least one antithrombotic agent, anticoagulant, antibiotic and/or antinflammatory agent.

In various embodiments, the restraining member, like the anchoring member and/or leaflet, may comprise at least on at least one radiopaque material that enhances its visibility under fluoroscopic imaging. Suitable materials include gold, barium sulfate, tantalum, palladium, and the like.

In various embodiments, the restraining member may contain surface features that make it convenient to capture and retrieve it with an interventional device such as a snare or grasper.

Kits

In various embodiments, a kit for implanting a prosthetic valve is provided, comprising:
an anchoring member having exterior and interior surfaces, the exterior surface of the anchoring member capable of contacting an inner wall of the body vessel, the interior surface of the anchoring member defining an opening for fluid flow in an antegrade and a retrograde direction;
at least one leaflet having a first edge attached to the anchoring member and a second edge being moveable between a first position and a second position, the first position substantially permits fluid flow in the antegrade direction and the second position substantially prevents the fluid flow in the retrograde direction; and a restraining member for contacting the second edge of the at least one leaflet, the restraining member capable of temporarily preventing substantial movement of the at least one leaflet between the first position and the second position so as to allow fluid flow in the antegrade and retrograde directions; packaging to maintain sterility of the implantable prosthetic valve.

In various embodiments, the kit includes packaging that keeps the valve free of water before implantation because many of the polymers are hydrolytically unstable, and the presence of moisture can degrade them in storage. A water free environment can be accomplished by quickly packaging the prosthetic valve after manufacture—generally double-bagged under an inert atmosphere or vacuum. The bag material may be polymeric or foil, but it must be highly resistant to water permeability. Packaged prosthetic devices should, preferably be kept at room temperature when opened to minimize condensation, and should be handled as little as possible at ambient atmospheric conditions. Final packaging consists of placing the prosthetic valve in an airtight, moisture proof container. A desiccant can be added to further reduce the effects of moisture.

In various embodiments, the prosthetic valve incorporating biodegradable polymers cannot be subjected to autoclaving, and must be sterilized by gamma or E-beam irradiation or by exposure to ethylene oxide (EtO) gas. The temperature and humidity conditions should also be considered when submitting valves for sterilization. Temperatures must be kept below the glass-transition temperature of the polymer to prevent the part geometry from changing during sterilization. If necessary, parts can be kept at 0° C. or lower during the irradiation process.

In various embodiments, the kit includes packaging that keeps the valve sterile before implantation.

In various embodiments, the kits may include certain accessories such as an annulus sizer, a valve holder, cutting devices, suturing devices and/or sutures, capture devices such as a snare or grasper or a capture device specifically designed to retrieve restraining members of a particular design, delivery system, (e.g., catheters and/or cannulas) and may include written, audio, audiovisual instructions and/or guidelines for implantation of the prosthetic valve.

In various embodiments, the kit comprises a delivery system that has the prosthetic valve loaded within the delivery system for implantation. Delivery systems for prosthetic valves placement are known in the art and typical include catheters, cannulas, tubes, guide wires that may employ any one or more of a variety of mechanisms and apparatuses for collapsing the prosthetic valve, translating them through the lumen of the vessel at the implant site, expanding the vessel and/or deploying the valves using e.g., stents and balloons. Many of such delivery systems are known in the art for use in cardiovascular applications. Access to the vessel (e.g., artery, vein, capillary) is either by surgical access, minimally invasive port access or by percutaneous access or by a combination thereof. The delivery of the valves may be aided by fluoroscopy, angioscopy, ultrasound, intravascular ultrasound (IVUS), magnetic resonance imaging, endoscopy, subfascial endoscopy or other imaging methods.

In various embodiments, the prosthetic valve is made where all the components are made of such materials and are constructed in such a process that placement, retrieval and/or visualization of the prosthetic valve is possible and convenient under magnetic resonance imaging (MRI).

Implanting the Prosthetic Valve

A method of implanting the prosthetic valve within a blood vessel at a desired position is provided, comprising a) providing the prosthetic valve which comprises: (i) an anchoring member having exterior and interior surfaces, the interior surface of the anchoring member defining an opening for blood flow in an antegrade and a retrograde direction; (ii) at least one leaflet having a first edge attached to the anchoring member and a second edge being moveable between a first position and a second position, the first position substantially permits blood flow in the antegrade direction and the second position substantially prevents blood flow in the retrograde direction; b) forming an opening in the blood vessel; c) inserting the valve through the formed opening and delivering it to the desired position at which the valve is to be implanted and implanting the valve so that the exterior surface of the anchoring member is substantially coincident with a portion of an inner wall of the blood vessel; d) restraining the second edge of the at least one leaflet with a restraining member to temporarily prevent substantial movement of the at least one leaflet between the first position and the second position so as to allow blood flow in the antegrade and retrograde directions; and e) preventing the formation of abnormal, potentially thrombogenic, flow patterns immediately after implantation at the implant site and allowing sufficient time for the vessel to heal at the site of implantation f) later removing the restraining member or allowing it to be removed by natural processes of the body environment over time so that the second edge of the leaflet is freed and becomes moveable between the first position to permit blood flow in the antegrade direction and the second position to substantially prevent blood flow in the retrograde direction.

In various embodiments, a method of implanting the prosthetic valve within a blood vessel at a desired position is provided, comprising a) providing the prosthetic valve which comprises: at least one leaflet having a first edge attachable to the vessel wall and a second edge being moveable between a first position and a second position, the first position substantially permits blood flow in the antegrade direction and the second position substantially prevents blood flow in the retrograde direction; b) forming an opening in the blood vessel; c) inserting the valve through the formed opening and delivering it to the desired position at which the valve is to be implanted and implanting the valve so that the at least one leaflet is attached to the inner wall of the blood vessel; d) restraining the second edge of the at least one leaflet with a restraining member to temporarily prevent substantial movement of the at least one leaflet between the first position and the second position so as to allow blood flow in the antegrade and retrograde directions; and e) preventing the formation of abnormal, potentially thrombogenic, flow patterns immediately after implantation at the implant site and allowing sufficient time for the vessel to heal at the site of implantation f) later removing the restraining member or allowing it to be removed by natural processes of the body environment over time so that the second edge of the leaflet is freed and becomes moveable between the first position to permit blood flow in the antegrade direction and the second position to substantially prevent blood flow in the retrograde direction.

The prosthetic valve can be implanted by conventional techniques known in the art, such where access to the vessel (e.g., artery, vein, capillary) is made either by surgical access, minimally invasive port access or by percutaneous access or by a combination thereof and the prosthetic valve is deployed at the desired implantation site. To aid in positioning either through direct observation of the vessel, or through videoscopic or echocardiogram assistance. In various embodiments, the defective native or defective prosthetic valve is removed or ablated before implantation of the new valve.

In various embodiments, the prosthetic valve is attached to the lumen of the vessel to provide a seal with the vessel so that there is substantially no leakage of fluid and the valve leaflets are restrained using the restraining member. The prosthetic valve implantation can be accomplished in one interventional, medical, and/or surgical procedure. With the restraining member in place, the leaflet—and the prosthetic valve—will not block retrograde flow as the free edge of the leaflet can not substantially move to the second or closed position, or in a multi-leaflet design, the free edges of the leaflet members can not coapt. The flow remains largely unchanged after the prosthesis is delivered into the blood vessel and thus no potentially thrombogenic flow changes are created. Further, cell deposition and tissue growth can progress on both the anchoring member and the leaflet, preferably covering their surface with endothelial cells and rendering these surfaces less thrombogenic. Ideally, the leaflet-restraining member remains in place until such remodeling is accomplished. After this period of approximately 4-8 weeks the leaflet-restraining member is removed naturally by the body or in a separate interventional, medical, percutaneous and/or surgical procedure allowing the free edge(s) of the leaflet to be released and the valve can perform its intended function of maintaining unidirectional flow (e.g., when open in substantially the antegrade direction and when closed substantially preventing retrograde flow).

In various embodiments, the valve can be used to treat endovascular diseases that occur when natural valves in veins have not developed or were damaged or destroyed by disease or trauma. An example of a disease that damages or destroys valves in deep veins is deep venous thrombosis. Another pathomechanism that leads to the loss of venous valve function is the dilatation of veins in venous varicosity. Traumatic injury of venous valves may follow intravenous vascular interventions or vein surgery.

FIG. 1 illustrates a partially sectional view of a body vessel with the prosthetic valve deployed within the vessel 10. The prosthetic valve comprises anchoring members 20, leaflet 40, and restraining members 30 that temporarily hold the leaflets open allowing both antegrade (forward) and retrograde (reverse) flow of fluid (indicated by the arrow in stage 1) through the opening. The exterior surface of the anchoring member 20 is attached to the lumen of the vessel 10 so that anchoring member is substantially flush with a portion of the lumen (not shown) or substantially coincident with the lumen (shown). This can be accomplished by any suitable means, for example, stent, suture, etc. as discussed above.

In FIG. 1, an edge of the leaflet 40 is attached to the interior surface of the anchoring member 20, by any suitable means, for example, suture, adhesives, heat sealing, tissue welding, weaving, cross-linking, etc. so that the leaflet has a free edge that moves between a first or open position and a second or closed position (shown in stage 2) in response to fluid pressure. A restraining member 30 is disposed between the free edge of the leaflet and the anchoring member or the inner wall of the vessel (not shown). The restraining member 30 may be any suitable restraining member, for example, adhesives, glue, ring, etc, as long as it restrains the leaflet and is capable of being removed by an intervention or naturally by the body. With the restraining member 30 in place, the leaflet—and the prosthetic valve—will not block retrograde flow as the free edge of the leaflet can not substantially move to the second or closed position, or in a multi-leaflet design in FIG. 1, the free edges of the leaflet members can not coapt. The flow remains largely unchanged after the prosthesis is deployed in the blood vessel and thus no potentially thrombogenic flow changes are created. Further, cell deposition and tissue growth can progress on both the anchoring member and the leaflet, preferably covering their surface with endothelial cells and rendering these surfaces less thrombogenic. Ideally, the leaflet-restraining member remains in place until such remodeling is accomplished.

After a period of time, e.g., approximately 4-8 weeks, the leaflet-restraining member 30 is removed naturally by the body or in a separate interventional, medical, percutaneous and/or surgical procedure allowing the free edge(s) of the leaflet 40 to be released and the valve can perform its intended function of maintaining unidirectional flow shown in stage 2 (e.g., when open, flow is in substantially in the antegrade direction and when closed retrograde flow is substantially prevented by the retrograde flow facing surface of the coapting leaflets as indicated by the arrows). In FIG. 1, the anchoring member 20 and the restraining member 30 are approximately the same size, however, other embodiments are envisioned.

Figure 2:
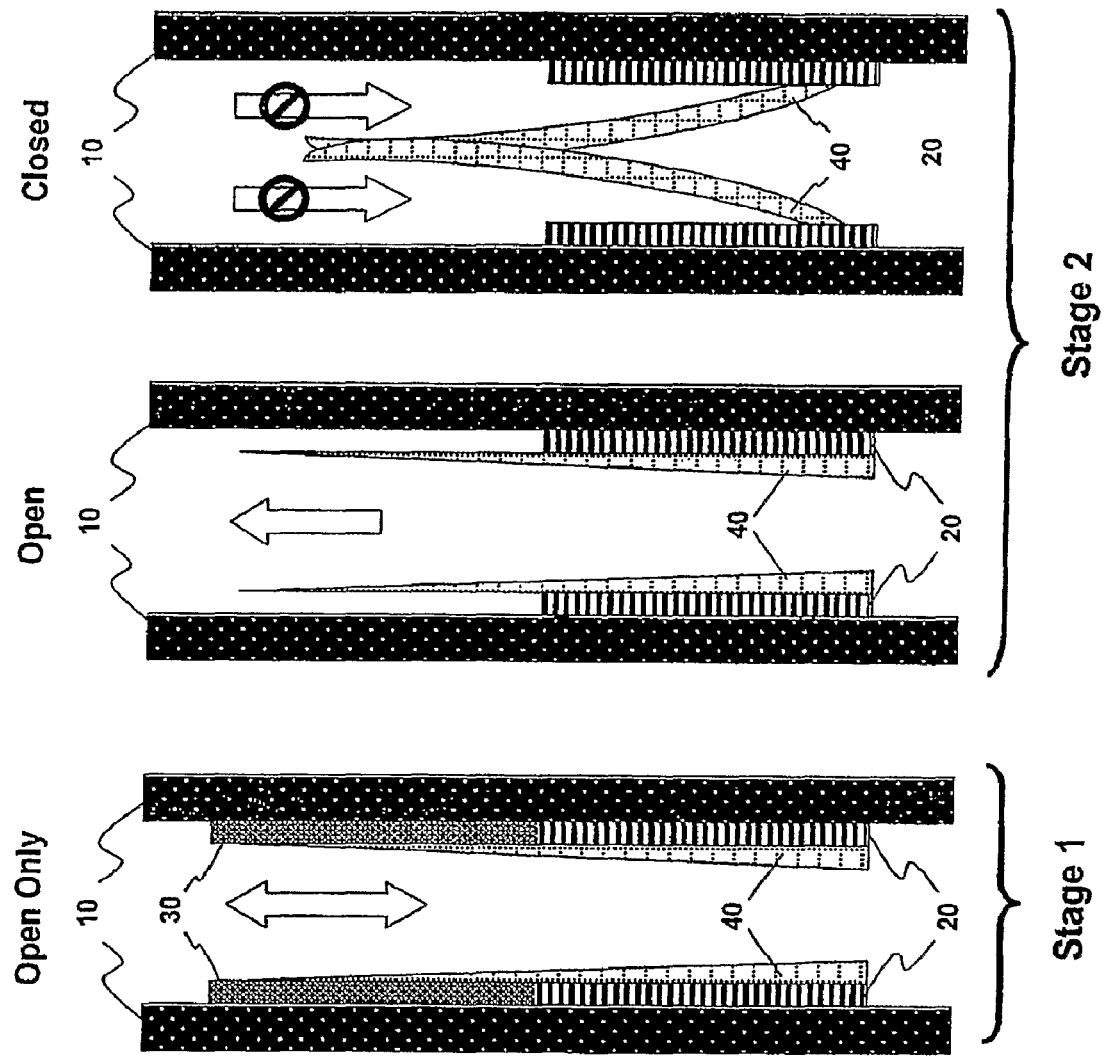
FIG. 2 illustrates a partially sectional view of a body vessel with the prosthetic valve implanted within the vessel 10. The prosthetic valve comprises anchoring members 20, leaflets 40, and restraining members 30 that temporarily hold the leaflets open allowing both antegrade and retrograde flow of fluid (indicated by the arrow in stage 1). This design reduces flow changes at the site of implantation while the at least one leaflet is restrained in the first position, and therefore reduces the appearance of potentially thrombogenic abnormal flow patterns, allows cell deposition making the valve more biocompatible, less thrombogenic before flow changes resulting from the at least one leaflet's valving action set in and allows tissue growth so that a partially or completely biological functioning valve may form on the scaffold provided by the implant. In this view, the anchoring members are shorter than the leaflets. In stage 2, after the restraining members 30 are removed (naturally by the body or through a procedure) the valve can now freely open and close as a native valve.

FIG. 2 illustrates a partially sectional view of a body vessel with the prosthetic valve implanted within the vessel 10. The prosthetic valve comprises anchoring members 20, leaflet members 40, and restraining members 30 that temporarily hold the leaflets open allowing both antegrade and retrograde flow of fluid (indicated by the arrow in stage 1). This design reduces flow changes at the site of implantation while the at least one leaflet is restrained in the first position, and therefore reduces the appearance of potentially thrombogenic abnormal flow patterns, allows cell deposition making the valve more biocompatible, less thrombogenic before flow changes resulting from the at least one leaflet's valving action set in and allows tissue growth so that a partially or completely biological functioning valve may form on the scaffold provided by the implant. In stage 2, after the restraining members 30 are removed (naturally by the body or in a separate interventional, medical, percutaneous and/or surgical procedure) the valve can now freely open and close as a native valve. In FIG. 2, the anchoring members 20 are shorter than the leaflets 40 and restraining members 30, however, other embodiments are envisioned.

Figure 3:
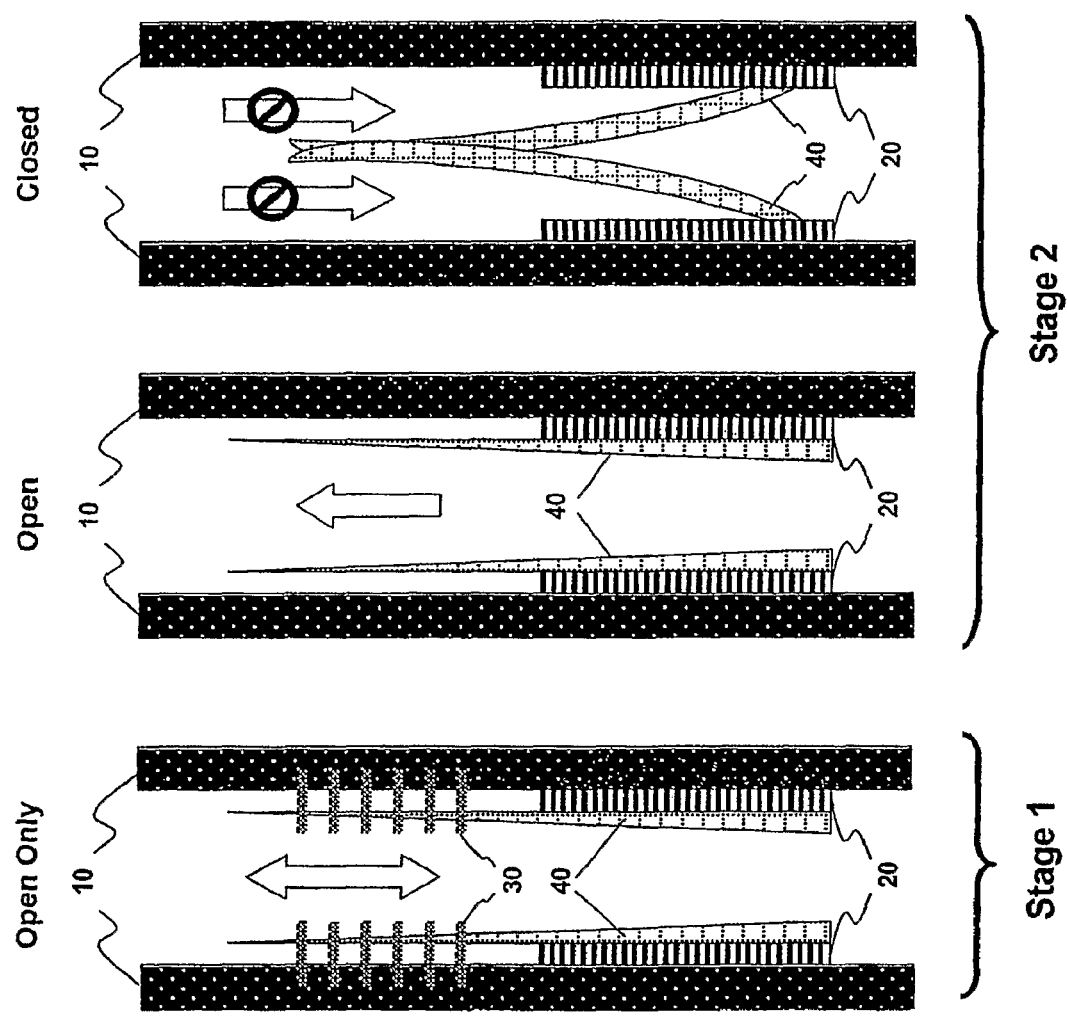
FIG. 3 illustrates a partially sectional view of a body vessel with the prosthetic valve implanted within the vessel 10. The prosthetic valve comprises anchoring members 20, leaflets 40, and restraining members 30 that temporarily hold the leaflets open allowing both antegrade and retrograde flow of fluid (indicated by the arrow in stage 1). This design reduces flow changes at the site of implantation while the at least one leaflet is restrained in the first position, and therefore reduces the appearance of potentially thrombogenic abnormal flow patterns, allows cell deposition making the valve more biocompatible, less thrombogenic before flow changes resulting from the at least one leaflet's valving action set in and allows tissue growth so that a partially or completely biological functioning valve may form on the scaffold provided by the implant. In this view, the restraining members (e.g., sutures, staples, clips, rivets) are positioned at the edge of the leaflets 40 and the anchoring member is shorter than the leaflets. In stage 2, after the restraining members 30 are removed (naturally by the body or through a procedure) the valve can now freely open and close as a native valve.

FIG. 3 illustrates a partially sectional view of a body vessel with the prosthetic valve implanted within the vessel 10. The prosthetic valve comprises anchoring members 26, leaflet members 40, and restraining members 30 that temporarily hold the leaflets open allowing both antegrade and retrograde flow of fluid (indicated by the arrow in stage 1). This design reduces flow changes at the site of implantation while the at least one leaflet is restrained in the first position, and therefore reduces the appearance of potentially thrombogenic abnormal flow patterns, allows cell deposition making the valve more biocompatible, less thrombogenic before flow changes resulting from the at least one leaflet's valving action set in and allows tissue growth so that a partially or completely biological functioning valve may form on the scaffold provided by the implant. In this view, the restraining members (e.g., sutures, staples, clips, rivets) are positioned at the edge of the leaflet 40. In stage 2, after the restraining members 30 are removed (naturally by the body or in a separate interventional, medical, percutaneous and/or surgical procedure) the valve can now freely open and close as a native valve. In FIG. 3, the anchoring members 20 are shorter than the leaflets 40, however, other embodiments are envisioned.

Figure 4:
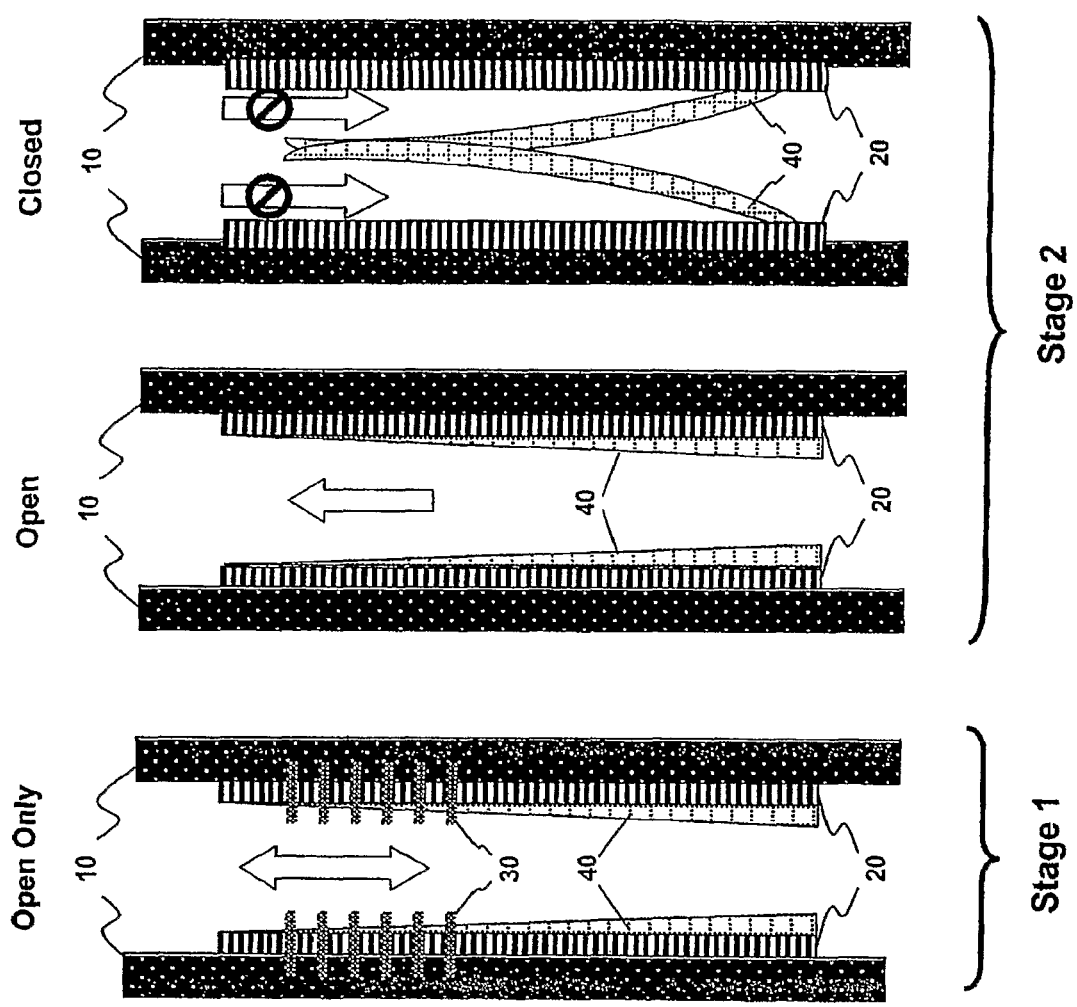
FIG. 4 illustrates a partially sectional view of a body vessel with the prosthetic valve implanted within the vessel 10. The prosthetic valve comprises anchoring members 20, leaflets 40, and restraining members 30 that temporarily hold the leaflets open allowing both antegrade and retrograde flow of fluid (indicated by the arrow in stage 1). This design reduces flow changes at the site of implantation while the at least one leaflet is restrained in the first position, and therefore reduces the appearance of potentially thrombogenic abnormal flow patterns, allows cell deposition making the valve more biocompatible, less thrombogenic before flow changes resulting from the at least one leaflet's valving action set in and allows tissue growth so that a partially or completely biological functioning valve may form on the scaffold provided by the implant. In this view, the restraining members (e.g., sutures, staples, clips, rivets) are positioned at the edge of the leaflets 40 and the anchoring members and leaflets are of similar length. In stage 2, after the restraining members 30 are removed (naturally by the body or through a procedure) the valve can now freely open and close as a native valve.

FIG. 4 illustrates a partially sectional view of a body vessel with the prosthetic valve implanted within the vessel 10. The prosthetic valve comprises anchoring members 20, leaflet members 40, and restraining members 30 that temporarily hold the leaflets open allowing both antegrade and retrograde flow of fluid (indicated by the arrow in stage 1). This design reduces flow changes at the site of implantation while the at least one leaflet is restrained in the first position, and therefore reduces the appearance of potentially thrombogenic abnormal flow patterns, allows cell deposition making the valve more biocompatible, less thrombogenic before flow changes resulting from the at least one leaflet's valving action set in and allows tissue growth so that a partially or completely biological functioning valve may form on the scaffold provided by the implant. In this view, the restraining members (e.g., sutures, staples, clips, rivets) are positioned at the edge of the leaflet 40. In stage 2, after the restraining members 30 are removed (naturally by the body or in a separate interventional, medical, percutaneous and/or surgical procedure) the valve can now freely open and close as a native valve. In FIG. 4, the anchoring members 20 are approximately the same length as the leaflets 40, however, other embodiments are envisioned.

Figure 5:
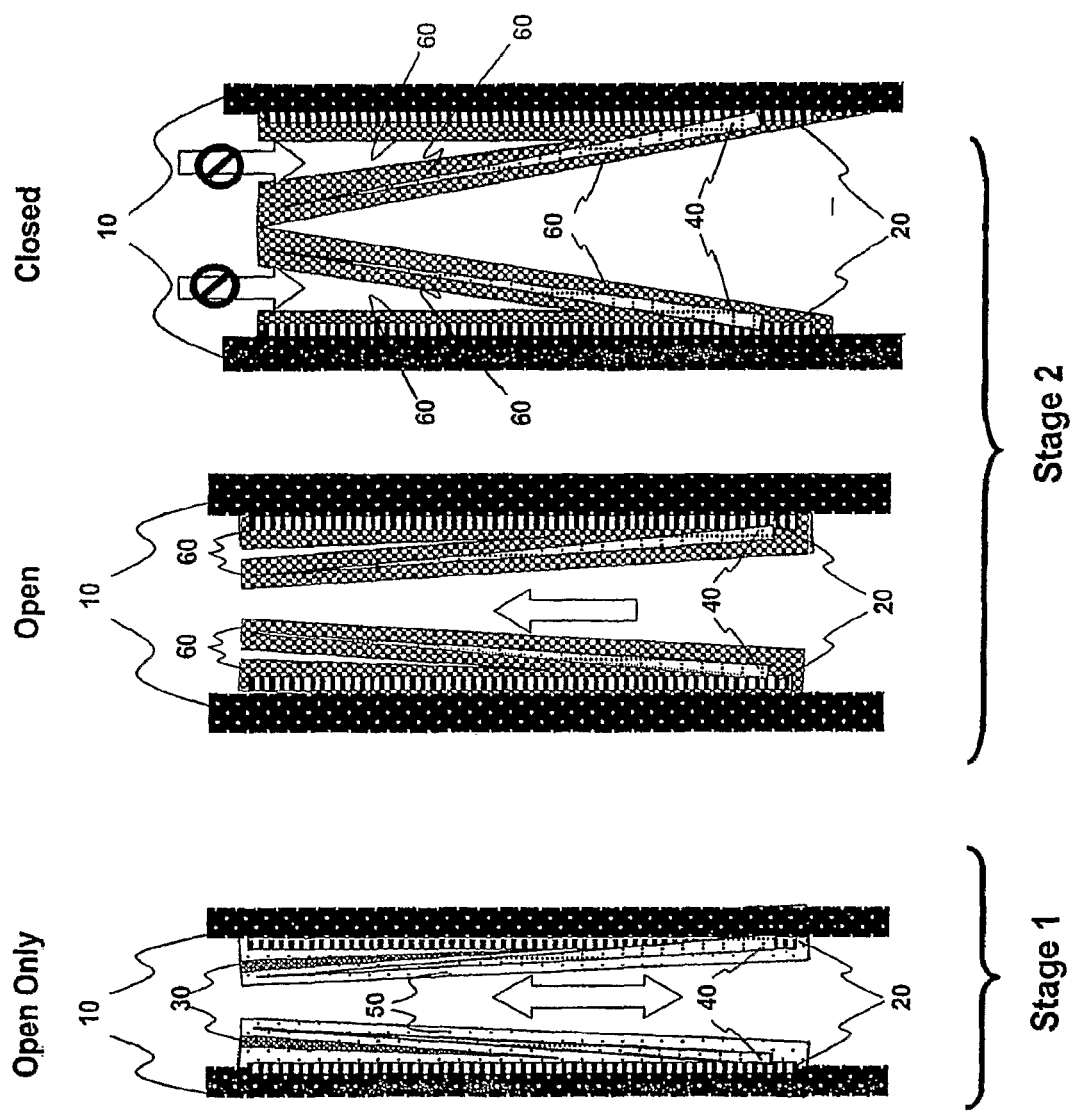
FIG. 5 illustrates a partially sectional view of a body vessel with the prosthetic valve implanted within the vessel 10. The prosthetic valve comprises anchoring members 20, leaflets 40, and restraining members 30 that temporarily hold the leaflets open allowing both antegrade and retrograde flow of fluid indicated by the arrow in stage 1. This design reduces flow changes at the site of implantation while the at least one leaflet is restrained in the first position, and therefore reduces the appearance of potentially thrombogenic abnormal flow patterns, allows cell deposition making the valve more biocompatible, less thrombogenic before flow changes resulting from the at least one leaflet's valving action set in and allows tissue growth so that a partially or completely biological functioning valve may form on the scaffold provided by the implant. The anchoring members 20 and leaflets have a substance disposed thereon (50) that enhances cellular growth. In stage 2, after the restraining members 30 are removed (naturally by the body or through a procedure) allowing the valve to open and close as a native valve. The anchoring members and leaflets have newly grown tissue disposed thereon (60) that replaces cellular growth prompting layer, which allows the valve to be more biocompatible and reduces the risk of thrombosis.

FIG. 5 illustrates a partially sectional view of a body vessel with the prosthetic valve implanted within the vessel 10. The prosthetic valve comprises anchoring members 20, leaflet members 40, and restraining members 30 that temporarily hold the leaflets open allowing both antegrade and retrograde flow of fluid indicated by the arrow in stage 1. This design reduces flow changes at the site of implantation while the at least one leaflet is restrained in the first position, and therefore reduces the appearance of potentially thrombogenic abnormal flow patterns, allows cell deposition making the valve more biocompatible, less thrombogenic before flow changes resulting from the at least one leaflet's valving action set in and allows tissue growth so that a partially or completely biological functioning valve may form on the scaffold provided by the implant. The anchoring members 20 and leaflets have a substance or surface disposed thereon (50) that enhance cellular growth. In stage 2, after the restraining members 30 are removed (naturally by the body or in a separate interventional, medical, percutaneous and/or surgical procedure) the valve can now freely open and close as a native valve. Shown in stage 2, the anchoring members 20 and leaflets 40 have newly grown tissue disposed thereon (60) that replaces the cellular growth substance, which allows the valve to be more biocompatible and reduces the risk of thrombosis. In FIG. 5, the anchoring members 20 are approximately the same length as the leaflets 40, however, other embodiments are envisioned where the leaflets are longer or shorter than the anchoring members and/or restraining members.

Figure 6:
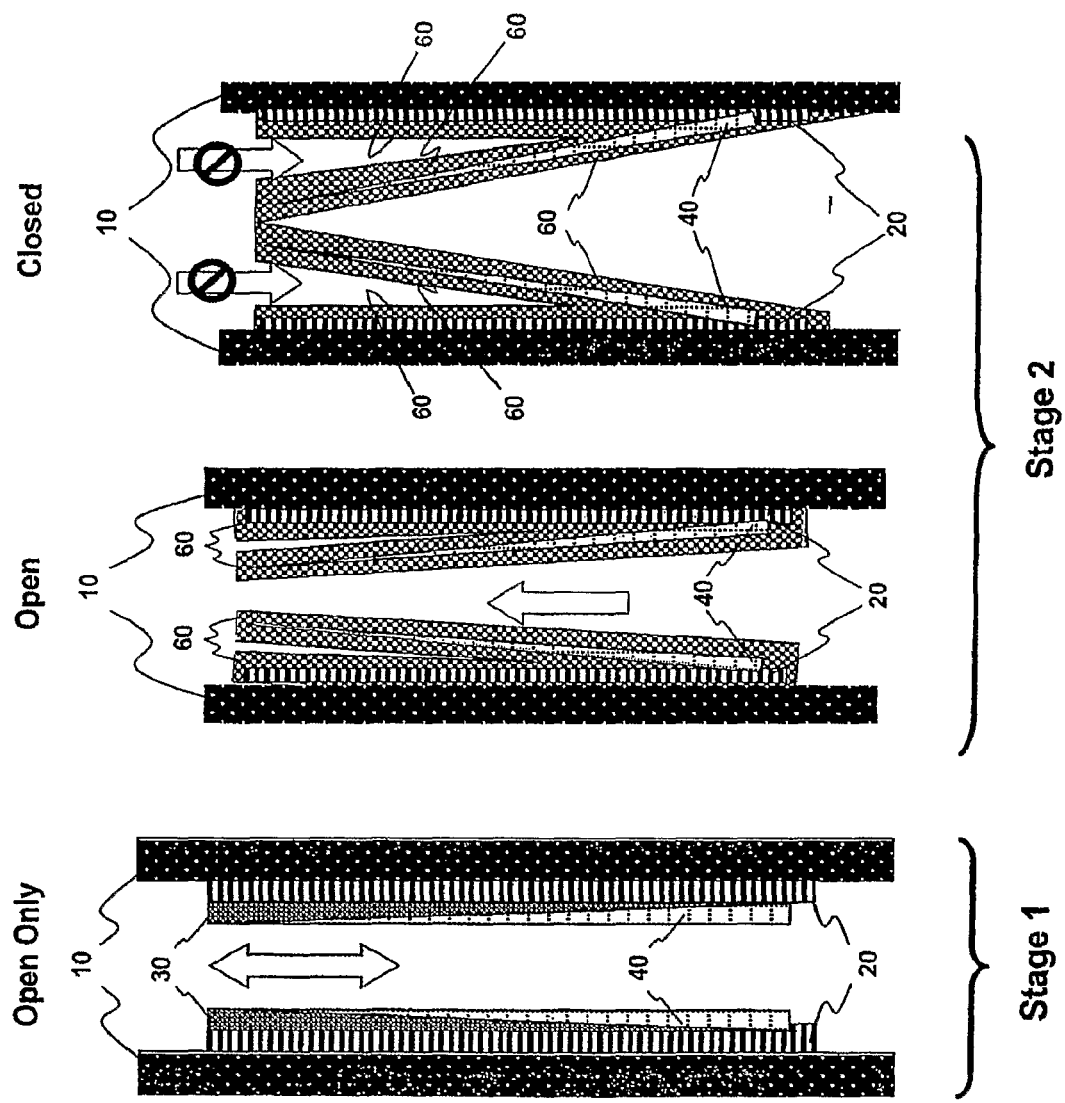
FIG. 6 illustrates a partially sectional view of a body vessel with the prosthetic valve implanted within the vessel 10. The prosthetic valve comprises anchoring members 20, leaflets 40, and restraining members 30 that temporarily hold the leaflets open allowing both antegrade and retrograde flow of fluid indicated by the arrow in stage 1. This design reduces flow changes at the site of implantation while the at least one leaflet is restrained in the first position, and therefore reduces the appearance of potentially thrombogenic abnormal flow patterns, allows cell deposition making the valve more biocompatible, less thrombogenic before flow changes resulting from the at least one leaflet's valving action set in and allows tissue growth so that a partially or completely biological functioning valve may form on the scaffold provided by the implant. In stage 2, after the restraining members 30 are removed (naturally by the body or through a procedure) allowing the valve to open and close as a native valve. The anchoring members and leaflets have newly grown tissue disposed thereon (60), which allows the valve to be more biocompatible and reduces the risk of thrombosis.

FIG. 6 illustrates a partially sectional view of a body vessel with the prosthetic valve implanted within the vessel 10. The prosthetic valve comprises anchoring members 20, leaflet members 40, and restraining members 30 that temporarily hold the leaflets open allowing both antegrade and retrograde flow of fluid (indicated by the arrow in stage 1). This design reduces flow changes at the site of implantation while the at least one leaflet is restrained in the first position, and therefore reduces the appearance of potentially thrombogenic abnormal flow patterns, allows cell deposition making the valve more biocompatible, less thrombogenic before flow changes resulting from the at least one leaflet's valving action set in and allows tissue growth so that a partially or completely biological functioning valve may form on the scaffold provided by the implant. In stage 2, after the restraining members 30 are removed (naturally by the body or in a separate interventional, medical, percutaneous and/or surgical procedure) the valve can now freely open and close as a native valve. Shown in stage 2, the anchoring members 20 and leaflets 40 have newly grown tissue disposed thereon (60), which allows the valve to be more biocompatible and reduces the risk of thrombosis. In FIG. 6, the anchoring members 20 are approximately the same length as the leaflets 40, however, other embodiments are envisioned where the leaflets are longer or shorter than the anchoring members and/or restraining members.

Figure 7:
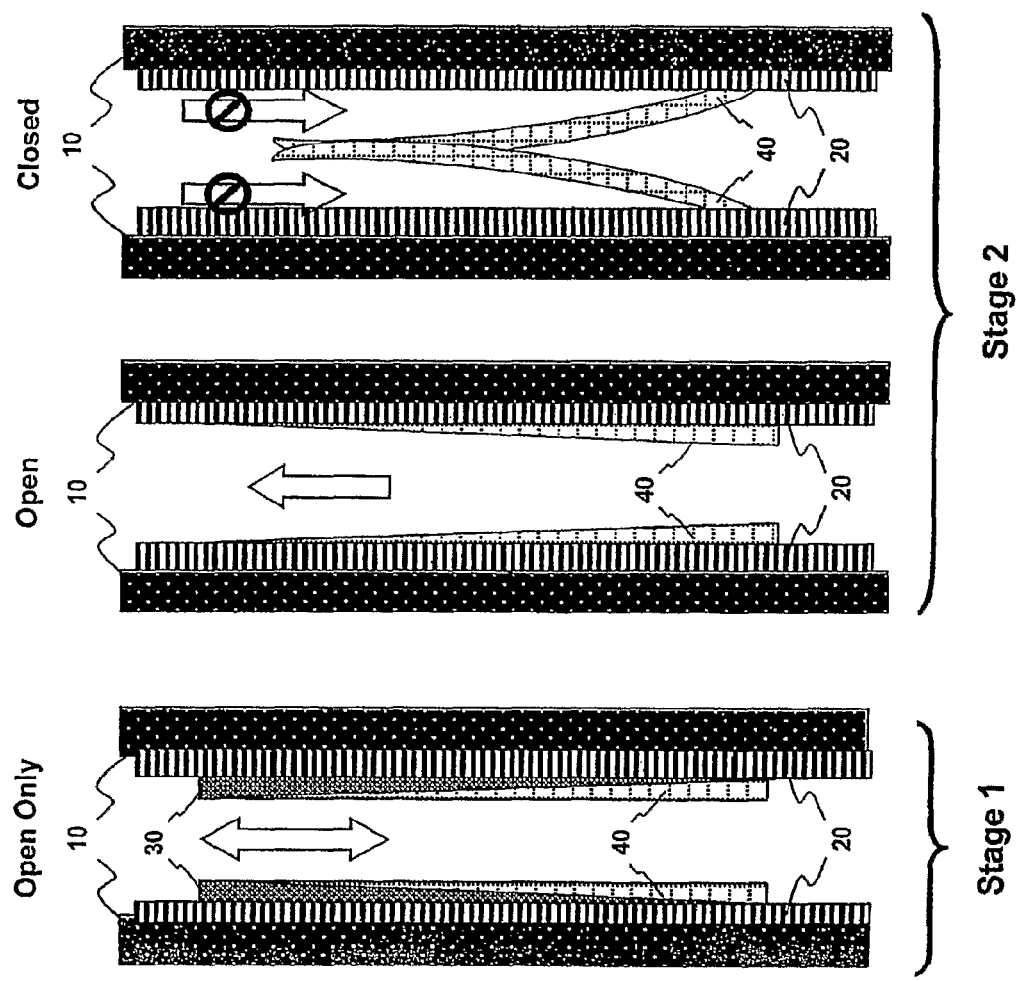
FIG. 7 illustrates a partially sectional view of a body vessel with the prosthetic valve implanted within the vessel 10. The prosthetic valve comprises anchoring members 20, leaflets 40, and restraining members 30 that temporarily hold the leaflets open allowing both antegrade (forward) and retrograde (reverse) flow of fluid (indicated by the arrow in stage 1). This design reduces flow changes at the site of implantation while the at least one leaflet is restrained in the first position, and therefore reduces the appearance of potentially thrombogenic abnormal flow patterns, allows cell deposition making the valve more biocompatible, less thrombogenic before flow changes resulting from the at least one leaflet's valving action set in and allows tissue growth so that a partially or completely biological functioning valve may form on the scaffold provided by the implant. In this view, the anchoring members and restraining members are longer than the leaflets. In stage 2, after the restraining members 30 are removed (naturally by the body or through a procedure) the valve can now freely open and close as a native valve.

FIG. 7 illustrates a partially sectional view of a body vessel with the prosthetic valve implanted within the vessel 10. The prosthetic valve comprises anchoring members 20, leaflets 40, and restraining members 30 that temporarily hold the leaflets open allowing both antegrade (forward) and retrograde (reverse) flow of fluid (indicated by the arrow in stage 1). This design reduces flow changes at the site of implantation while the at least one leaflet is restrained in the first position, therefore reduces the appearance of potentially thrombogenic abnormal flow patterns, allows cell deposition making the valve more biocompatible, less thrombogenic before flow changes resulting from the at least one leaflet's valving action set in and allows tissue growth so that a partially or completely biological functioning valve may form on the scaffold provided by the implant. In this view, the anchoring members and restraining members are longer than the leaflets. In stage 2, after the restraining members 30 are removed (naturally by the body or through a procedure) the valve can now freely open and close as a native valve. In FIG. 7, the restraining members 30 and anchoring members 20 are longer than the leaflets 40, however, other embodiments are envisioned, where the leaflets are the same length or longer than the anchoring members and/or restraining members.

Figure 8:
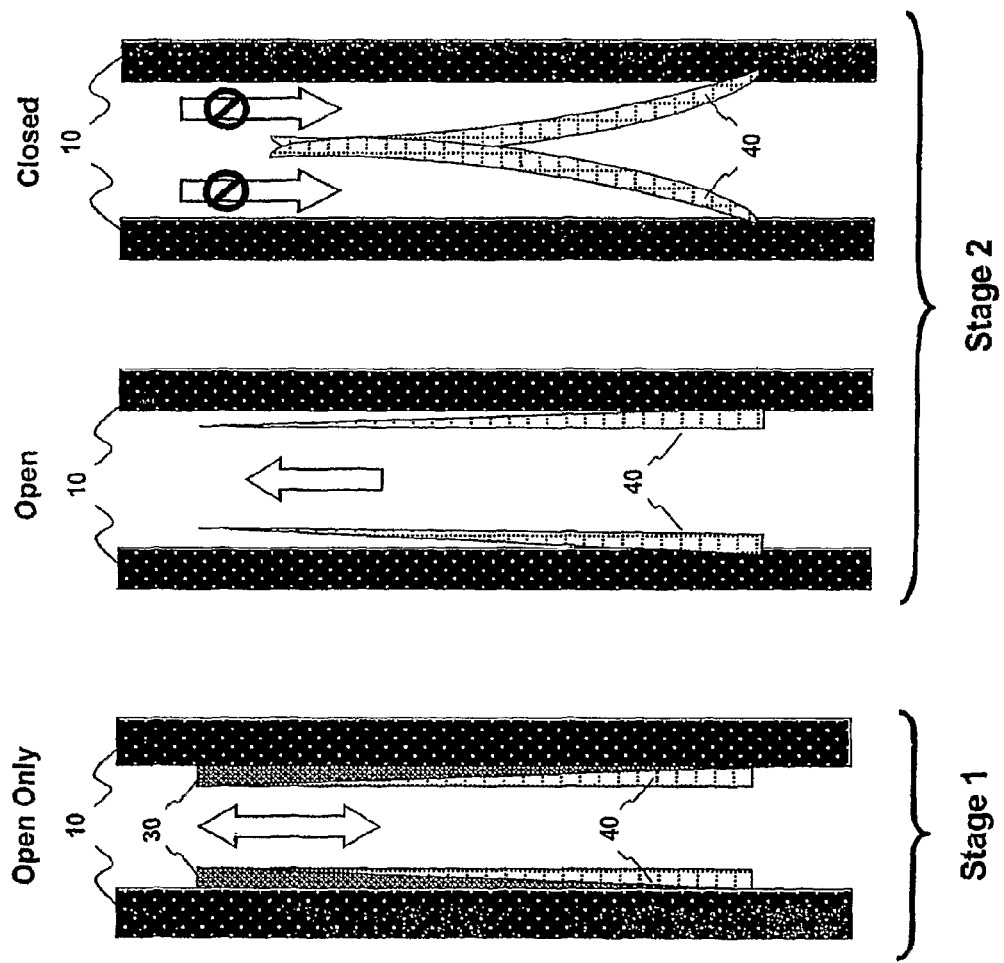
FIG. 8 illustrates a partially sectional view of a body vessel with the prosthetic valve implanted within the vessel 10. The prosthetic valve comprises leaflets 40, and restraining members 30 that temporarily hold the leaflets open allowing both antegrade (forward) and retrograde (reverse) flow of fluid (indicated by the arrow in stage 1). This design reduces flow changes at the site of implantation while the at least one leaflet is restrained in the first position, and therefore reduces the appearance of potentially thrombogenic abnormal flow patterns, allows cell deposition making the valve more biocompatible, less thrombogenic before flow changes resulting from the at least one leaflet's valving action set in and allows tissue growth so that a partially or completely biological functioning valve may form on the scaffold provided by the implant. In stage 2, after the restraining members 30 are removed (naturally by the body or through a procedure) the valve can now freely open and close as a native valve.

FIG. 8 illustrates a partially sectional view of a body vessel with the prosthetic valve implanted within the vessel 10. The prosthetic valve comprises leaflets 40, and restraining members 30 that temporarily hold the leaflets open allowing both antegrade (forward) and retrograde (reverse) flow of fluid (indicated by the arrow in stage 1). This design reduces flow changes at the site of implantation while the at least one leaflet is restrained in the first position, therefore reduces the appearance of potentially thrombogenic abnormal flow patterns, allows cell deposition making the valve more biocompatible, less thrombogenic before flow changes resulting from the at least one leaflet's valving action sets in and allows tissue growth so that a partially or completely biological functioning valve may form on the scaffold provided by the implant. In stage 2, after the restraining members 30 are removed (naturally by the body or through a procedure) the valve can now freely open and close as a native valve. In FIG. 8, the anchoring members 20 are approximately the same length as the leaflets 40, however, other embodiments are envisioned, where the leaflets are shorter or longer than the restraining members.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. An implantable prosthetic valve for regulating fluid flow through a body vessel, comprising:
    an anchoring member having exterior and interior surfaces, the exterior surface of the anchoring member capable of contacting an inner wall of the body vessel, the interior surface of the anchoring member defining an opening for fluid flow in an antegrade and a retrograde direction;
    at least one leaflet having a first edge attached to the anchoring member and a second edge being moveable between a first position and a second position, the first position substantially permits fluid flow in the antegrade direction and the second position substantially prevents the fluid flow in the retrograde direction; and
    a restraining member contacting the second edge of the at least one leaflet, the anchoring member, and/or vessel wall, the restraining member capable of temporarily preventing substantial movement of the at least one leaflet between the first position and the second position so as to allow fluid flow in the antegrade and retrograde directions;
    wherein the restraining member is sized to be left within the blood vessel after implantation of the valve and closure of an implantation site to thereby prevent substantial movement of the at least one leaflet for a sufficient length of time to allow endothelial tissue overgrowth of one or both of the at least one leaflet and the anchoring member.

2. An implantable prosthetic valve according to claim 1, wherein the restraining member holds the at least one leaflet in the first position to allow the at least one leaflet and anchoring member to be overgrown, after the valve is implanted, by tissue cells deposited from the blood flow and/or migrating from surrounding tissue to make the valve more biocompatible and to resist blood clotting on or near the surface of the implanted prosthetic valve.

3. An implantable prosthetic valve according to claim 2, wherein when the restraining member is removed or released, the at least one leaflet when in the first position substantially permits fluid flow in the antegrade direction and when in the second position substantially prevents the fluid flow in the retrograde direction as a native valve.

4. An implantable prosthetic valve for regulating fluid flow through a body vessel, comprising:
    an anchoring member having exterior and interior surfaces, the exterior surface of the anchoring member capable of contacting an inner wall of the body vessel, the interior surface of the anchoring member defining an opening for fluid flow in an antegrade and a retrograde direction;
    at least one leaflet having a first edge attached to the anchoring member and a second edge being moveable between a first position and a second position, the first position substantially permits fluid flow in the antegrade direction and the second position substantially prevents the fluid flow in the retrograde direction; and
    a restraining member contacting the second edge of the at least one leaflet, the anchoring member, and/or vessel wall, the restraining member capable of temporarily preventing substantial movement of the at least one leaflet between the first position and the second position so as to allow fluid flow in the antegrade and retrograde directions;
    wherein the restraining member contacts the second edge of the leaflet and the interior surface of the anchoring member.

5. An implantable prosthetic valve according to claim 1, wherein the anchoring member and/or at least one leaflet is coated with a substance that prompts cellular or tissue growth, after the valve is implanted, by tissue cells deposited from the blood flow or migrating from surrounding tissue to make the valve more biocompatible and to resist blood clotting on or near the surface of the implanted valve prosthetic valve.

6. An implantable prosthetic valve according to claim 1, wherein the anchoring member further comprises a support frame having radially compressed and radially expanded configurations.

7. An implantable prosthetic valve according to claim 1, wherein the anchoring member, the at least one leaflet, and/or restraining member comprises at least one metal, biological material, biocompatible material, bioremodellable material, bioabsorbable material, a synthetic material, or combinations thereof.

8. An implantable prosthetic valve according to claim 1, wherein the anchoring member, the restraining member and/or the at least one leaflet comprises at least one anti-thrombogenic agent, anticoagulant, antibiotic, antinflammatory agent or a combination thereof.

9. An implantable prosthetic valve for regulating fluid flow through a body vessel, comprising:
   an anchoring member having exterior and interior surfaces, the exterior surface of the anchoring member capable of contacting an inner wall of the body vessel, the interior surface of the anchoring member defining an opening for fluid flow in an antegrade and a retrograde direction;
   at least one leaflet having a first edge attached to the anchoring member and a second edge being moveable between a first position and a second position, the first position substantially permits fluid flow in the antegrade direction and the second position substantially prevents the fluid flow in the retrograde direction; and
   a restraining member contacting the second edge of the at least one leaflet, the anchoring member, and/or vessel wall, the restraining member capable of temporarily preventing substantial movement of the at least one leaflet between the first position and the second position so as to allow fluid flow in the antegrade and retrograde directions;
   wherein the at least one leaflet:
      i) is substantially coincident with all or a portion of the interior surface of the anchoring member;
      ii) is shorter than the anchoring member;
      or iii) is longer than the anchoring member and the restraining member contacts the vessel wall.

10. An implantable prosthetic valve according to claim 1, wherein a surface of the at least one leaflet coapts with the inner wall of the body vessel when in the second position to substantially prevent fluid flow in the retrograde direction.

11. An implantable prosthetic valve according to claim 1, wherein the prosthetic valve comprises at least two or three leaflets, each leaflet comprising coapting surfaces when in the second position to substantially prevent fluid flow in the retrograde direction.

12. An implantable prosthetic valve for regulating fluid flow through a body vessel, comprising:
   an anchoring member having exterior and interior surfaces, the exterior surface of the anchoring member capable of contacting an inner wall of the body vessel, the interior surface of the anchoring member defining an opening for fluid flow in an antegrade and a retrograde direction;
   at least one leaflet having a first edge attached to the anchoring member and a second edge being moveable between a first position and a second position, the first position substantially permits fluid flow in the antegrade direction and the second position substantially prevents the fluid flow in the retrograde direction; and
   a restraining member contacting the second edge of the at least one leaflet, the anchoring member, and/or vessel wall, the restraining member capable of temporarily preventing substantial movement of the at least one leaflet between the first position and the second position so as to allow fluid flow in the antegrade and retrograde directions;
   wherein the restraining member is degradable.

13. An implantable prosthetic valve for regulating fluid flow through a body vessel, comprising:
   an anchoring member having exterior and interior surfaces, the exterior surface of the anchoring member capable of contacting an inner wall of the body vessel, the interior surface of the anchoring member defining an opening for fluid flow in an antegrade and a retrograde direction;
   at least one leaflet having a first edge attached to the anchoring member and a second edge being moveable between a substantially open position and a substantially closed position, the open position substantially permits fluid flow and the closed position substantially prevents fluid flow; and
   a restraining member contacting the second edge of the at least one leaflet, the restraining member capable of temporarily holding the at least one leaflet in the substantially open position to allow fluid flow;
   wherein the restraining member is sized to be left within the blood vessel after implantation of the valve and closure of an implantation site to thereby prevent substantial movement of the at least one leaflet for a sufficient length of time to allow endothelial tissue overgrowth of one or both of the at least one leaflet and the anchoring member.

14. An implantable prosthetic valve according to claim 13, wherein when the restraining member is removed fluid flow in an antegrade direction moves the at least one leaflet in the open position and fluid flow in the retrograde direction moves the at least one leaflet in the closed position.

15. A kit for implanting a prosthetic valve, comprising:
   an anchoring member having exterior and interior surfaces, the exterior surface of the anchoring member capable of contacting an inner wall of the body vessel, the interior surface of the anchoring member defining an opening for fluid flow in an antegrade and a retrograde direction;
   at least one leaflet having a first edge attached to the anchoring member and a second edge being moveable between a first position and a second position, the first position substantially permits fluid flow in the antegrade direction and the second position substantially prevents the fluid flow in the retrograde direction;
   a restraining member for contacting the second edge of the at least one leaflet, the anchoring member and/or vessel, the restraining member capable of temporarily preventing substantial movement of the at least one leaflet between the first position and the second position so as to allow fluid flow in the antegrade and retrograde directions;
   wherein the restraining member is sized to be left within the blood vessel after implantation of the valve and closure of an implantation site to thereby prevent substantial movement of the at least one leaflet for a sufficient length of time to allow endothelial tissue overgrowth of one or both of the at least one leaflet and the anchoring member;
   packaging for the implantable prosthetic valve; and
   instructions for implanting the prosthetic valve.

16. A kit for implanting a prosthetic valve according to claim 15, further comprising a delivery system and the prosthetic valve is compressed within the delivery system.

17. An implantable prosthetic valve leaflet for regulating fluid flow through a body vessel, the leaflet comprising a first edge and a second edge, the first edge capable of being attached to a wall of the body vessel, and/or an anchoring member, the second edge of the leaflet having a restraining member capable of temporarily restraining the second edge of the leaflet against the wall of the body vessel and/or anchoring member so as to substantially prevent movement of the leaflet between a first position and a second position.

18. A method of implanting a prosthetic valve within a blood vessel at a desired position therein, comprising:
   a) providing a prosthetic valve which comprises:
      (i) an anchoring member having exterior and interior surfaces, the interior surface of the anchoring member defining an opening for blood flow in an antegrade and a retrograde direction;
      (ii) at least one leaflet having a first edge attached to the anchoring member and a second edge being moveable between a first position and a second position, the first position substantially permits blood flow in the antegrade direction and the second position substantially prevents blood flow in the retrograde direction;
   b) forming an opening in the blood vessel;
   c) inserting the valve through the formed opening and delivering the valve to the desired position at which the valve is to be implanted and implanting the valve so that the exterior surface of the anchoring member is substantially coincident with a portion of an inner wall of the blood vessel;
   d) restraining the second edge of the at least one leaflet with a restraining member to temporarily prevent substantial movement of the at least one leaflet between the first position and the second position so as to allow blood flow in the antegrade and retrograde directions;
   e) allowing the vessel to heal after the valve is implanted; and
   f) later removing the restraining member or allowing the restraining member to be removed by the body so that the second edge of the leaflet is moveable between the first position to permit blood flow in the antegrade direction and the second position to substantially prevent blood flow in the retrograde direction.

19. A method of implanting a prosthetic valve according to claim 18, wherein step f) is performed after growth of endothelial cells on the anchoring member and the at least one leaflet.

20. A method of implanting a prosthetic valve according to claim 18, wherein i) step b) or c) further comprise removing a defective native or defective prosthetic valve; ii) the at least one leaflet, anchoring member, and restraining member comprise a double walled tube; and/or iii) the anchoring member and/or at least one leaflet comprises at least one growth or adhesion factor that enhance cellular growth.

21. A method of implanting a prosthetic valve according to claim 18, further comprising step g) removing the entire prosthetic valve or at least one leaflet in a separate procedure.

22. A method of implanting a prosthetic valve within a blood vessel at a desired position therein, comprising:
   a) providing a prosthetic valve which comprises at least one leaflet having a first edge attached to the vessel wall and a second edge being moveable between a first position and a second position, the first position substantially permits blood flow in the antegrade direction and the second position substantially prevents blood flow in the retrograde direction;
   b) forming an opening in the blood vessel;
   c) inserting the valve through the formed opening and delivering the valve to the desired position at which the valve is to be implanted and implanting the valve so that the first edge of the leaflet is attached to the inner wall of the blood vessel;
   d) restraining the second edge of the at least one leaflet with a restraining member to temporarily prevent substantial movement of the at least one leaflet between the first position and the second position so as to allow blood flow in the antegrade and retrograde directions;
   e) allowing the vessel to heal after the valve is implanted; and
   f) later removing the restraining member or allowing the restraining member to be removed by the body so that the second edge of the leaflet is moveable between the first position to permit blood flow in the antegrade direction and the second position to substantially prevent blood flow in the retrograde direction.

23. A method of implanting a prosthetic valve according to claim 22, wherein step f) is performed after growth of endothelial cells on the at least one leaflet.

24. A method of implanting a prosthetic valve according to claim 22, wherein i) step b) or c) further comprise removing a defective native or defective prosthetic valve; ii) the at least one leaflet, and restraining member comprise a double walled tube; and/or iii) the at least one leaflet comprises at least one growth or adhesion factor that enhance cellular growth.

25. A method of implanting a prosthetic valve according to claim 22, further comprising step g) removing the entire prosthetic valve or at least one leaflet in a separate procedure.

* * * * *